United States Patent
Kanbara et al.

(10) Patent No.: US 12,060,311 B2
(45) Date of Patent: Aug. 13, 2024

(54) METHOD FOR PRODUCING AROMATIC NITRILE BY AMMOXIDATION REACTION

(71) Applicant: MITSUBISHI GAS CHEMICAL COMPANY, INC., Chiyoda-ku (JP)

(72) Inventors: Yutaka Kanbara, Niigata (JP); Yuta Oomori, Kamisu (JP); Yoichi Kyuuko, Niigata (JP); Tomoo Tsujimoto, Chiyoda-ku (JP); Kazunari Yamamoto, Niigata (JP); Tsuyoshi Hatakeyama, Kurashiki (JP)

(73) Assignee: MITSUBISHI GAS CHEMICAL COMPANY, INC., Chiyoda-ku (JP)

( * ) Notice: Subject to any disclaimer, the term of this patent is extended or adjusted under 35 U.S.C. 154(b) by 1025 days.

(21) Appl. No.: 16/970,581

(22) PCT Filed: Mar. 18, 2019

(86) PCT No.: PCT/JP2019/011026
§ 371 (c)(1),
(2) Date: Aug. 17, 2020

(87) PCT Pub. No.: WO2019/188459
PCT Pub. Date: Oct. 3, 2019

(65) Prior Publication Data
US 2021/0107864 A1    Apr. 15, 2021

(30) Foreign Application Priority Data
Mar. 30, 2018  (JP) ................. 2018-067764

(51) Int. Cl.
C07C 253/28   (2006.01)
B01J 21/02    (2006.01)
B01J 21/06    (2006.01)
B01J 23/26    (2006.01)
B01J 23/28    (2006.01)

(52) U.S. Cl.
CPC ............ *C07C 253/28* (2013.01); *B01J 21/02* (2013.01); *B01J 21/063* (2013.01); *B01J 23/26* (2013.01); *B01J 23/28* (2013.01)

(58) Field of Classification Search
CPC .................................................. C07C 253/28
See application file for complete search history.

(56) References Cited

U.S. PATENT DOCUMENTS 7,161,044 B2 *  1/2007  Nakamura ............ C07C 45/35
                                                562/521
2005/0209484 A1  9/2005  Shin et al.
2013/0310604 A1  11/2013 Kurakami et al.

FOREIGN PATENT DOCUMENTS

| GB | 351 523       | 5/1974 |
| JP | 11-209332 A   | 8/1999 |
| JP | 2003-267942 A | 9/2003 |
| JP | 2012-176938 A | 9/2012 |

OTHER PUBLICATIONS

A machine generated English translation of JP 2003-267942 A (Ebata et al.) , 2003. (Year: 2003).*
Extended European Search Report issued Apr. 15, 2021 in European Patent Application No. 19776597.7, 7 pages.
International Search Report issued on Jun. 18, 2019 in PCT/JP2019/011026 filed on Mar. 18, 2019, 1 page.
Japanese Office Action issued on Mar. 7, 2023 in Japanese Patent Application No. 2020-510677 with unedited computer-generated English translation, 6 pages.

* cited by examiner

*Primary Examiner* — Laura L Stockton
(74) *Attorney, Agent, or Firm* — Oblon, McClelland, Maier & Neustadt, L.L.P.

(57) ABSTRACT

The present invention can provide a method for producing an aromatic nitrile in which a fixed-bed reactor including a plurality of reaction tubes is used to subject a gaseous mixture comprising an aromatic hydrocarbon, ammonia, and oxygen by contact catalytic reaction on a catalyst to thereby produce the corresponding aromatic nitrile, wherein the catalyst is composed of an oxide containing vanadium, chromium, and boron and one or more supports selected from among alumina, silica-alumina, zirconia, and titania. One of the reaction tubes is filled with the catalyst of one kind and examined as to where a hot spot lies therein. An inert substance is filled into that portion of each of the plurality of reaction tubes which corresponds at least to the hot spot, and the catalyst is filled into the remaining portions.

18 Claims, 5 Drawing Sheets

METHOD FOR PRODUCING AROMATIC NITRILE BY AMMOXIDATION REACTION

TECHNICAL FIELD

The present invention relates to a method for producing an aromatic nitrile by allowing contact reaction of a gaseous mixture containing an aromatic hydrocarbon, ammonia and oxygen on a catalyst. The aromatic nitrile is useful as a material used for producing a synthetic resin, a pesticide or the like and as an intermediate for amine, isocyanate or the like.

BACKGROUND ART

Reaction of an aromatic hydrocarbon with ammonia and oxygen in a gas phase is called ammoxidation reaction, for which various processes have been proposed. Examples of the reaction system for ammoxidation include a fixed bed system and a fluidized bed system. Since ammoxidation reaction generates a large amount of reaction heat, it is very difficult to control the reaction temperature. One solution for this is reaction employing the fluidized bed system, which has been considered effective and thus various processes have been proposed therefor. For example, a method that uses a catalyst with a silica support (Patent document 1) shows good performance in controlling the reaction temperature. None of these catalysts, however, can avoid abrasion and erosion of the catalyst in the fluid state, and thus it is difficult to maintain the reaction stable. Furthermore, a fluidized bed system requires a step of separating the gas and the catalyst after the reaction, which increases the cost and thus unfavorable.

Meanwhile, a multitubular reactor is used for the fixed bed system, which requires improvement of efficiency in removing the reaction heat. In general, a metal oxide catalyst having an active component supported on alumina or titania is used. As such an active catalyst, an oxide of vanadium, chromium, antimony, molybdenum, tin, boron or the like, or a complex oxide thereof can be used. With a known catalyst, however, an increase in the byproducts such as carbon dioxide and hydrogen cyanide due to acceleration of combustion reaction caused by local overheating, specifically, due to difficulty in controlling the reaction temperature, causes problems including a decrease in the yield of the product of interest, i.e., an aromatic nitrile.

Moreover, when an exothermic reaction is carried out in a fixed bed, a part that has the locally highest temperature, i.e., a hot spot, occurs and causes a side reaction or a runaway reaction that may have a risk of exceeding the heat-resistant temperature of the apparatus. Accordingly, there has been a need for a method for suppressing such hot spot.

PRIOR ART DOCUMENTS

Patent Documents

Patent document 1: Japanese Unexamined Patent Application Publication No. Heisei 11-209332

SUMMARY OF THE INVENTION

Problems to be Solved by the Invention

The present invention aims at suppressing a part having the locally highest temperature, i.e., a hot spot, upon producing an aromatic nitrile by ammoxidation reaction using a fixed-bed reactor, and at enabling a stable operation without a side reaction or a runaway reaction.

Means for Solving the Problems

In order to solve the above-described problem, the present inventors have gone through intensive studies, and as a result of which found that said problem can be solved by filling inert substance to a part of the reaction tube where there is a hot spot, thereby accomplishing the present invention.

Thus, the present invention is as follows.

<1> A method for producing an aromatic nitrile by using a fixed-bed reactor including a plurality of reaction tubes to allow contact reaction of a gaseous mixture containing an aromatic hydrocarbon, ammonia and oxygen on a catalyst to produce the corresponding aromatic nitrile, wherein:
the catalyst is composed of an oxide containing vanadium, chromium and boron, and one or more supports selected from alumina, silica-alumina, zirconia and titania; and
one of the reaction tube is filled with the catalyst of one kind to identify the site of a hot spot, and then, for each of the plurality of reaction tubes, a part corresponding at least to said hot spot is filled with inert substance while a part other than that is filled with the catalyst.

<2> A method for producing an aromatic nitrile by using a fixed-bed reactor including a plurality of reaction tubes to allow contact reaction of a gaseous mixture containing an aromatic hydrocarbon, ammonia and oxygen on a catalyst to produce the corresponding aromatic nitrile, wherein:
the catalyst is composed of an oxide containing vanadium, chromium and boron, and one or more supports selected from alumina, silica-alumina, zirconia and titania; and
one of the reaction tube is filled with the catalyst of one kind to identify the site of a hot spot, and then, for each of the plurality of reaction tubes, a part corresponding at least to said hot spot is filled with a mixture of the catalyst and inert substance while a part other than that is filled with the catalyst.

<3> A method for producing an aromatic nitrile by using a fixed-bed reactor including a plurality of reaction tubes to allow contact reaction of a gaseous mixture containing an aromatic hydrocarbon, ammonia and oxygen on a catalyst to produce the corresponding aromatic nitrile, wherein:
the catalyst is composed of an oxide containing vanadium, chromium and boron, and one or more supports selected from alumina, silica-alumina, zirconia and titania; and
one of the reaction tube is filled with the catalyst of one kind to identify the site of a hot spot, and then, for each of the plurality of reaction tubes, a part corresponding at least to said hot spot is filled with the catalyst while a part other than that is filled with a catalyst free of boron or a catalyst having less amount of boron than said catalyst.

<4> A method for producing an aromatic nitrile by using a fixed-bed reactor including a plurality of reaction tubes to allow contact reaction of a gaseous mixture containing an aromatic hydrocarbon, ammonia and oxygen on a catalyst to produce the corresponding aromatic nitrile, wherein:

the catalyst is composed of an oxide containing vanadium, chromium and boron, and one or more supports selected from alumina, silica-alumina, zirconia and titania; and one of the reaction tube is filled with the catalyst of one kind to identify the site of a hot spot, and then, for each of the plurality of reaction tubes, a part corresponding at least to said hot spot is filled with one catalyst having a lower calcination temperature of the catalysts of two kinds having different calcination temperatures while a part other than that is filled with the other catalyst having a higher calcination temperature.

<5> The method for producing an aromatic nitrile according to any one of <1> to <4> above, wherein the oxide containing vanadium, chromium and boron is represented by the following composition formula:

Composition formula $V_aCr_bB_cX_dO_e$

[wherein, V represents vanadium, Cr represents chromium, B represents boron, X represents one type of element selected from phosphorus, molybdenum, iron, tungsten, germanium, manganese, tin, tantalum, niobium, antimony, bismuth, lead, tellurium, cobalt, nickel, sodium, potassium, rubidium, cesium, magnesium, calcium and barium, O represents oxygen, and subscripts a, b, c, d and e represent the atomic ratios of respective elements where a is 1, b is 0.5-2.0, c is 0.01-1.5, d is 0-2.0 and e represents the oxygen number corresponding to an oxide or a complex oxide formed by binding said elements].

<6> The method for producing an aromatic nitrile according to any one of <1> to <5> above, wherein the support is titania.

<7> The method for producing an aromatic nitrile according to any one of <2> to <6> above, wherein the part corresponding at least to said hot spot refers to a part including the inlet of the reaction tube to the hot spot.

<8> The method for producing an aromatic nitrile according to any one of <2> to <7> above, wherein the amount of the catalyst in the part corresponding at least to said hot spot is 0.6 or less provided that the weight of the whole catalyst bed in the reaction tube is 1.

Advantageous Effect of the Invention

The present invention can suppress hot spots and enable a stable operation without causing a side reactions or a runaway reaction upon producing an aromatic nitrile by an ammoxidation reaction using a fixed-bed reactor.

EMBODIMENTS FOR CARRYING OUT THE INVENTION

Hereinafter, embodiments for carrying out the present invention (hereinafter, simply referred to as "embodiments") will be described in detail, although the present invention should not be limited thereto. The present invention may be modified in various ways without departing from the scope thereof.

The present invention comprise the following Embodiments 1-4, where they shape common requirement that they are "a method for producing an aromatic nitrile by using a fixed-bed reactor including a plurality of reaction tubes to allow contact reaction of a gaseous mixture containing an aromatic hydrocarbon, ammonia and oxygen on a catalyst to produce the corresponding aromatic nitrile, wherein: the catalyst is composed of an oxide containing vanadium, chromium and boron, and one or more supports selected from alumina, silica-alumina, zirconia and titania; and one of the reaction tube is filled with the catalyst of one kind to identify the site of a hot spot".

Examples of the aromatic hydrocarbon used as a raw material in the present invention include alkyl benzenes such as toluene and ethyl benzene; polyalkyl benzenes such as such as xylene, mesitylene, cymene, durene and diethyl benzene; alkyl naphthalenes such as methyl naphthalene and ethyl naphthalene; and polyalkyl naphthalenes such as dimethyl naphthalene and diethyl naphthalene, which are hydrocarbon compounds having a carbon ring such as benzene or naphthalene, and having at least one side chain (hereinafter, referred to as a substituent) that can generate a cyano group via an ammoxidation reaction, for example, a methyl group, an ethyl group, a propyl group, a formyl group, an acetyl group, a hydroxymethyl group, a methoxycarbonyl group or the like bound thereto. Moreover, these hydrocarbon compounds may contain a halogen group, a hydroxy group, an alkoxyl group, an amino group, a nitro group, a nitrile group or the like. These compounds may be used alone or as a mixture.

Ammonia used in the present invention may be an industrial grade product. The amount of ammonia used is 1-20 molar times, preferably 3-15 molar times that of a substituent contained in 1 mole of the aromatic hydrocarbon. The yield of the product of interest will be decreased if the amount used is smaller than this, whereas the space-time yield will be decreased if the amount is larger than this. According to the method of the present invention, unreacted ammonia contained in the reaction gas can be collected and returned to the reaction system to be reused. While unreacted ammonia can be collected from the reaction gas in various ways, it is industrially advantageous to allow water to absorb the unreacted ammonia, and then separate ammonia from other byproducts by a distillation operation. While the amount of moisture contained in the ammonia to be collected at this point varies depending on the conditions of the distillation operation, it usually contains 5-20 vol % moisture.

Oxygen used in the present invention is supplied in a form of oxygen-containing gas, where air is usually used. As an alternative method, air or oxygen can be diluted in inert gas, for example, nitrogen, carbon dioxide, emitted gas or the like, to be used. The amount of oxygen used in terms of $O_2$ is 1.5 molar times or more, preferably 2-50 molar times that of a substituent contained in 1 mole of the aromatic hydrocarbon. The yield of the product of interest will be decreased if the amount used is smaller than this, whereas the space-time yield will be decreased if the amount is larger than this.

The catalyst used in the present invention is composed of an oxide containing vanadium, chromium and boron (hereinafter, also referred to as a "metal oxide"), and one or more supports selected from alumina, silica-alumina, zirconia and titania.

The metal oxide may be added with other component and may contain, for example, two or more types of elements selected from phosphorus, molybdenum, iron, tungsten, germanium, manganese, tin, tantalum, niobium, antimony, bismuth, lead, tellurium, cobalt, nickel, sodium, potassium, rubidium, cesium, magnesium, calcium and barium.

The metal oxide is preferably represented by the following composition formula.

Composition formula $V_aCr_bB_cX_dO_e$

[wherein, V represents vanadium, Cr represents chromium, B represents boron, X represents one type of element selected from phosphorus, molybdenum, iron, tungsten, germanium, manganese, tin, tantalum, niobium, antimony, bismuth, lead, tellurium, cobalt, nickel, sodium, potassium, rubidium, cesium, magnesium, calcium and barium, O represents oxygen, and subscripts a, b, c, d and e represent the atomic ratios of respective elements where a is 1, b is 0.5-2.0, c is 0.01-1.5, d is 0-2.0 and e represents the oxygen number corresponding to an oxide or a complex oxide formed by binding said elements].

X is preferably molybdenum, phosphorus, sodium or potassium, and particularly preferably molybdenum.

Examples of the support include alumina, silica-alumina, zirconia and titania, where titania is preferable among them.

The amount of the support is preferably 50-99 wt % and more preferably 65-97 wt % in the catalyst.

While ammonium metavanadate, vanadyl sulfate and vanadium salts of organic acids such as oxalic acid and tartaric acid can be used as a vanadium source of the catalyst, ammonium metavanadate, vanadyl oxalate, vanadyl tartrate or the like is preferable since they can be decomposed and easily be turned into an oxide in the subsequent calcination operation.

While chromic anhydride, chromium nitrate, chromium hydrate, ammonium chromate, sodium chromate, ammonium dichromate, potassium dichromate, sodium dichromate and chromium salts of organic acids such as oxalic acid and tartaric acid can be used as a chromium source, chromium oxalate, chromium tartrate or the like is preferable since they can be decomposed and easily be turned into an oxide in the subsequent calcination operation.

Boric acid, ammonium borate or the like can be used as a boron source.

The catalyst used in the present invention can be produced by employing the following method.

Aqueous solutions of the compounds used as the vanadium source, the chromium source and the boron source and, if necessary, additional compounds are mixed to prepare a homogeneous aqueous solution, to which a support is added and mixed.

For example, an aqueous solution of chromic anhydride in oxalic acid and an aqueous borate solution are added to an aqueous solution of vanadium oxide in oxalic acid to give a homogeneous aqueous solution, to which alumina or titania powder as a support is added and mixed. Subsequently, the resultant is mechanically kneaded to facilitate sufficient homogenization of the catalyst.

After kneading, the resultant is dried at 110° C.-150° C. and then pulverized to give powder. Here, prior to pulverization, the dried product is preferably pre-fired at 250° C.-500° C., more preferably at 270° C.-450° C.

Then, the powder is mechanically compressed and further fired to prepare a catalyst.

First, the powder is molded into a suitable shape by a molding machine. The shape of the catalyst is preferably a column, a ring, a sphere, a trefoil, a quatrefoil or the like, and particularly preferably a column or a ring. While the molding machine may be an extrusion molding machine, a tumbling granulator, a tableting machine or the like, a tableting machine is most preferable in order to obtain a sufficiently robust catalyst. If a tableting machine is to be used, a molding auxiliary agent (binder) such as graphite or ethyl cellulose is preferably added upon compressing the powder. The amount added is preferably 1%-10%. Molding is followed by firing at 350° C.-800° C., preferably at 400° C.-700° C. for a few hours or longer while allowing air flow.

The catalyst is preferably shaped to have a size of an outer diameter of 3 mm-8 mm and a height of 3 mm-8 mm.

The reaction system that uses the catalyst prepared by the above-described method is usually a gas-phase flow fixed-bed system. The reaction apparatus is generally a filled-bed catalytic reactor, which is filled with catalyst particles so that the raw material gas (a gaseous mixture containing an aromatic hydrocarbon, ammonia and oxygen) can undergo continuous reaction thereon.

While the modes of heat transfer in filled-bed a catalytic reactors can be classified roughly into a heat insulating mode and a heat exchanging mode, a heat exchange reactor is preferable since the reaction of the present invention is an exothermic reaction. Especially, a single-tube or multitubular heat exchange reactor is preferable, in which the reaction tube is filled with the catalyst and the heat medium runs outside the tube.

While the material of the reactor depends on the types of the raw materials and the reaction conditions, in general, it is preferably stainless steel, carbon steel or the like.

Figure 1:
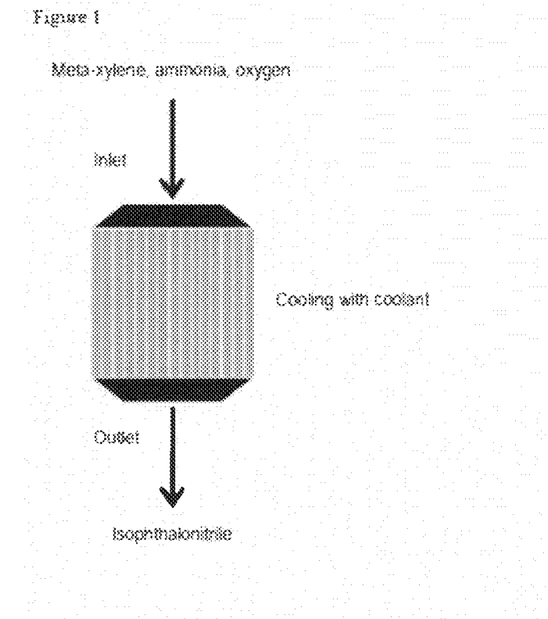
FIG. 1 A schematic view showing an exemplary fixed-bed reactor including a plurality of reaction tubes used in the present invention.

While the fixed-bed reactor used in the present invention includes a plurality of reaction tubes, the number of the reaction tubes is generally about 20,000-100,000, and preferably 20,000-50,000. FIG. 1 is a schematic view showing an exemplary fixed-bed reactor of the present invention including a plurality of reaction tubes. In FIG. 1, meta-xylene is used as the aromatic hydrocarbon.

The reaction tube preferably has a diameter of 1 cm to 5 cm and a length of 10 cm to 7 m.

While the reaction can take place at a temperature widely ranging from 300° C. to 600° C., it preferably takes place at 330° C.-500° C. The conversion rate of the raw material compound will be low at a temperature lower than 300° C., whereas generation of carbon dioxide, hydrogen cyanide and the like is increased and thus the yield of the nitrile compound will be decreased at a temperature higher than 600° C. The heat medium is particularly preferably a molten salt for use at high temperature. Since the reaction temperature that can give the highest yield varies depending on the types of the raw materials, the concentrations of the raw materials, the contact time, the calcination temperature of the catalyst and the like, the temperature is preferably selected within the above-mentioned range in accordance with such conditions. Generally, the contact time between the raw material gas and the catalyst ranges quite broadly but it is preferably 0.5-30 seconds.

While the reaction of the present invention usually takes place at atmospheric pressure, it may also be carried out under pressure or at reduced pressure. The reaction product can be collected by employing any suitable method, for example, a method in which the product is sufficiently cooled to a temperature that causes deposition so that the product can be collected, or a method in which the gaseous reaction product is washed with water or any other solvent so that the product can be collected.

As to the method for producing an aromatic nitrile by an ammoxidation reaction according to the present invention, a reaction formula where meta-xylene is used as the aromatic hydrocarbon is shown below.

Meta-xylene

Isophthalonitrile

Additionally to the above-described common subject matter, Embodiment 1 of the present invention is characterized in that "for each of the plurality of reaction tubes, a part corresponding at least to said hot spot is filled with inert substance while a part other than that is filled with the catalyst".

Herein, when one of the reaction tubes is filled entirely with one type of the catalysts, the "part corresponding at least to said hot spot" comprises not only a part of the reaction tube locally having the highest temperature (hot spot) but also a part without the hot spot which is slightly off said hot spot.

Specifically, if the above-described hot spot is located at 0.3 provided that the weight of the whole catalyst bed in the reaction tube is 1, the "part corresponding at least to said hot spot" also comprises a part starting from 0.4 (for example, 0.4-0.6).

Although the amount of the inert substance in the "part corresponding at least to said hot spot" varies depending on the material used, it is, for example, preferably 0.001-0.9 and more preferably 0.01-0.8 provided that the weight of the whole catalyst bed in the reaction tube is 1.

While the inert substance used in Embodiment 1 of the present invention is not particularly limited as long as it can suppress excessive exothermic reaction, it is preferably a ring, pellets, a ball or the like made from a metal oxide such as a ceramic or a metal, more preferably a ceramic ring or ball.

Additionally to the above-described common subject matter, Embodiment 2 of the present invention is characterized in that "for each of the plurality of reaction tubes, a part corresponding at least to said hot spot is filled with a mixture of the catalyst and inert substance while a part other than that is filled with the catalyst".

According to Embodiment 2 of the present invention, the "part corresponding at least to said hot spot" is preferably a part including the inlet of the reaction tube to the hot spot.

According to Embodiment 2 of the present invention, the amount of the catalyst in the "part corresponding at least to said hot spot" is preferably 0.6 or less and more preferably 0.55 or less provided that the weight of the whole catalyst bed in the reaction tube is 1. The amount of the catalyst here refers to the amount of the mixture of the catalyst and inert substance.

The inert substance used in Embodiment 2 of the present invention may be the same as that used in Embodiment 1 of the present invention.

In Embodiment 2 of the present invention, the ratio of the catalyst to the inert substance is preferably 0.05:1-20:1 and more preferably 0.1:1-10:1 in a weight ratio.

Here, instead of filling the "part corresponding to the hot spot" with a mixture of the catalyst and the inert substance, the front layer preceding the hot spot may be filled with the mixture of the catalyst and inert substance while the back layer following the front layer (the hot spot is included in this back layer) may be filled with the catalyst.

Additionally to the above-described common subject matter, Embodiment 3 of the present invention is characterized in that "for each of the plurality of reaction tubes, a part corresponding at least to said hot spot is filled with the catalyst while a part other than that is filled with a catalyst free of boron or a catalyst having less amount of boron than said catalyst".

In Embodiment 3 of the present invention, the "part corresponding at least to said hot spot" preferably includes the inlet of the reaction tube to the hot spot.

According to Embodiment 3 of the present invention, the amount of the catalyst in the "part corresponding at least to said hot spot" is preferably 0.6 or less and more preferably 0.55 or less provided that the weight of the whole catalyst bed in the reaction tube is 1. The amount of the catalyst here refers to the amount of the catalyst containing boron or the catalyst having larger amount of boron than the other.

Here, instead of filling the "part corresponding to the hot spot" with the catalyst, the front layer preceding the hot spot may be filled with the catalyst while the back layer following the front layer (the hot spot is included in this back layer) may be filled with a catalyst free of boron or a catalyst having less amount of boron than said catalyst.

Additionally to the above-described common subject matter, Embodiment 4 of the present invention is characterized in that "for each of the plurality of reaction tubes, a part corresponding at least to said hot spot is filled with one catalyst having a lower calcination temperature of the catalysts of two kinds having different calcination temperatures while a part other than that is filled with the other catalyst having a higher calcination temperature".

In Embodiment 4 of the present invention, the "part corresponding at least to said hot spot" preferably includes the inlet of the reaction tube to the hot spot.

According to Embodiment 4 of the present invention, the amount of the catalyst in the "part corresponding at least to said hot spot" is preferably 0.6 or less and more preferably 0.55 or less provided that the weight of the whole catalyst bed in the reaction tube is 1. The amount of the catalyst here refers to the amount of the catalyst having a lower calcination temperature.

Difference in the calcination temperature between the catalysts of two kinds in Embodiment 4 of the present invention is preferably 10° C.-150° C. and more preferably 20° C.-100° C.

Here, instead of filling the "part corresponding to the hot spot" with one catalyst having a lower calcination temperature of the catalysts of two kinds having different calcination temperatures, the front layer preceding the hot spot may be filled with the catalyst having a lower calcination temperature while the back layer following the front layer (the hot spot is included in this back layer) may be filled with the other catalyst having a higher calcination temperature.

EXAMPLES

Hereinafter, the present invention will be described by way of examples, although the present invention should not be limited in any way to these examples.

<Preparation of Catalyst A>

196 g of chromic anhydride $CrO_3$ was dissolved in 200 mL of pure water to prepare an aqueous chromic acid solution. Then, 600 mL of pure water was added to 753 g of oxalic acid and the resultant was heated to 50° C.-60° C. to prepare an aqueous oxalic acid solution. The aqueous chromic acid solution was slowly added to this aqueous oxalic acid solution while stirring to prepare an aqueous chromium oxalate solution.

Meanwhile, 444 g of oxalic acid was dissolved in 400 mL of pure water, and the resultant was heated to 80° C.-90° C. To this, 178 g of vanadium pentoxide $V_2O_5$ was slowly added while stirring thoroughly to prepare an aqueous vanadyl oxalate solution. Then, the aqueous chromium oxalate solution prepared above was dropped into the aqueous vanadyl oxalate solution prepared above at 70° C.-90° C. to be mixed therewith. 12.1 g of boric acid was added to this mixed aqueous solution at 70° C.-90° C. to be mixed therewith. The thus-prepared catalyst solution was heated and matured at 85° C.-95° C. Subsequently, the resultant was concentrated at 100° C.-110° C. 1333 g of anatase titanium oxide was added to the concentrated liquid preparation, and the resultant was kneaded with a kneader at 70° C. until the resultant was homogeneous while evaporating the moisture. Thereafter, the resulting cake was dried with a drier at 110° C.

Next, the dried product was pre-fired in a firing furnace at 400° C. for 2 hours, and then pulverized with a pulverizer. The pulverized powder was added and mixed with graphite (4 wt %). Then, the resulting raw material power was tableted with a tableting machine into a ring shape having an outer diameter of 5.7 mm, an inner diameter of 2.4 mm and a height of 5.8 mm. After tableting, the resultant was fired in the firing furnace at 600° C. for 15 hours. This catalyst had an atomic ratio Cr:V:B of 1.0:1.0:0.1, and an composition formula $V_1Cr_1B_{0.1}O_x$ (wherein, x is a number corresponding to the metal oxide), where the concentration of titania as the support in the catalyst was 80 wt %.

<Preparation of Catalyst B>

A catalyst was prepared in the same manner as Catalyst A except that 21.0 g of $MoO_3$ was added simultaneously with boric acid.

<Preparation of Catalyst C>

A catalyst was prepared in the same manner as Catalyst A except that boric acid was not added.

<Preparation of Catalyst D>

A catalyst was prepared in the same manner as Catalyst A except that the calcination temperature was 650° C. instead of 600° C.

Comparative Example 1

Figure 2:
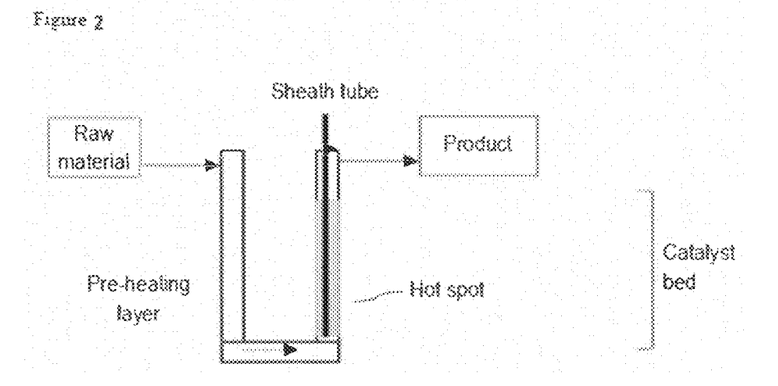
FIG. 2 A schematic view of a reaction tube used in Comparative example 1.

As shown in FIG. 2, a SUS304 U-shaped reaction tube having an inner diameter of 20 mm and a height of 500 mm was prepared, where the descending section of the reaction tube on the inlet side served as a pre-heating layer while the ascending section of the reaction tube on the outlet side served as a catalyst bed, and a sheath tube having an outer diameter of 2 mm was inserted therein so that a tip of a thermocouple can be moved up and down inside the reaction tube across the catalyst bed to measure the temperature thereof.

Next, Catalyst A was pulverized into eight with pliers, and fractionated with a sieve having openings of 1.25 mm followed by another sieve having openings of 0.95 mm to prepare pulverized Catalyst A having sizes of 0.95-1.25 mm. Then, the catalyst bed was filled entirely with 10 g of the pulverized Catalyst A.

The reaction tube was placed in a molten salt bath that was kept at 398° C., and the pipes on the inlet side and the outlet side of the reaction tube were heated and kept warm with a heater. Raw materials, namely, meta-xylene at 1.95 g/hr, ammonia at 2.45 g/hr, air at 155 Nml/min and nitrogen at 390 Nml/min, were introduced into the reaction tube at atmospheric pressure to allow contact reaction thereof. The gaseous reaction product was absorbed by tetrahydrofuran and analyzed with GC-2010 gas chromatograph manufactured by Shimadzu Corporation and column DB-1 having a length of 60 m, a thickness of 0.25 micrometers and an inner diameter of 0.25 mm (manufactured by Agilent Technologies) using tridecane as an internal standard under the following conditions: helium carrier gas at 15 ml/min; inlet temperature at 235° C.; split ratio of 11; FID detector at 235° C.; column temperature kept at 120° C. for 5 minutes and then raised to 230° C. at 40° C./min and kept there for 10 minutes; and injection volume of 1 microliter. As a result of the analysis, the meta-xylene conversion rate was 91%, and the isophthalonitrile yield was 71%.

In the catalyst bed shown in FIG. 2, a hot spot occurred at the part indicated as so. The hot spot was located in the vicinity of 0.31 provided that the weight of the whole catalyst bed in the reaction tube was 1. The hot spot temperature, namely, the highest temperature of the catalyst bed was 447° C. The results are summarized in Table 1 below.

Example 1

Figure 3:
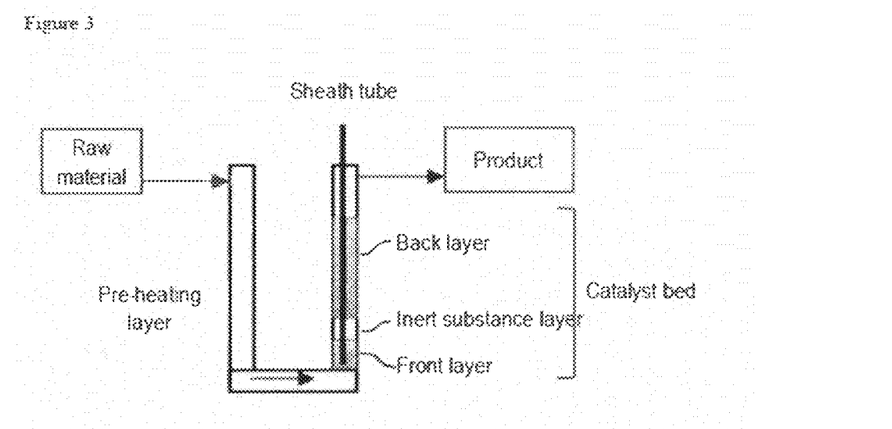
FIG. 3 A schematic view of a reaction tube used in Examples 1-4.

As shown in FIG. 3, a plurality of SUS304 U-shaped reaction tubes each having an inner diameter of 20 mm and a height of 500 mm were prepared, where the descending section of the reaction tube on the inlet side served as a pre-heating layer while the ascending section of the reaction tube on the outlet side served as a catalyst bed, and a sheath tube having an outer diameter of 2 mm was inserted therein so that a tip of a thermocouple can be moved up and down inside the reaction tube across the catalyst bed to measure the temperature thereof.

Next, Catalyst A prepared above was pulverized into eight with pliers, and fractionated with a sieve having openings of 1.25 mm followed by another sieve having openings of 0.95 mm to prepare pulverized Catalyst A having sizes of 0.95-1.25 mm. In the catalyst bed, a front layer as the first layer was filled with 2 g of the pulverized Catalyst A, an inert substance layer as the second layer (corresponding to the hot spot site identified in Comparative example 1) was filled with 12 g of ceramic raschig rings as inert substance each having an outer diameter of 3 mm, an inner diameter of 1 mm and a height of 2.5 mm (manufactured by Sakaguchi E.H Voc Corp.), and a back layer as the third layer was filled with 8 g of the pulverized Catalyst A. The inert substance was filled from the location at 0.2 provided that the weight of the whole catalyst in the front layer and the back layer was 1.

An activity test was conducted in the same manner as Comparative example 1 except that the molten salt bath was kept at 404° C. As a result, the meta-xylene conversion rate was 92% and the isophthalonitrile yield was 69%.

The temperature inside the catalyst bed became high in the first layer (front layer), then become low in the second layer (inert substance layer), and a hot spot having the highest temperature in the catalyst bed was caused in the third layer (back layer). The hot spot temperature was 439° C. The results are summarized in Table 1 below.

Example 2

The catalyst bed was filled with a catalyst in the same manner as Example 1 except that a front layer as the first layer was filled with 3 g of the pulverized Catalyst A, a back layer as the third layer was filled with 7 g of the pulverized Catalyst A, and the inert substance was filled from the location at 0.3 provided that the weight of the whole catalyst in the front layer and the back layer was 1.

An activity test was conducted in the same manner as Example 1 except that the molten salt bath was kept at 402° C. As a result, the meta-xylene conversion rate was 91% and the isophthalonitrile yield was 68%.

A hot spot having the highest temperature in the catalyst bed was caused in the first layer (front layer), and the temperature inside the catalyst bed became low in the second layer (inert substance layer), and became high and then low in the third layer (back layer). The hot spot temperature was 429° C. The results are summarized in Table 1 below.

Example 3

The catalyst bed was filled with a catalyst in the same manner as Example 1 except that a front layer as the first layer was filled with 4 g of the pulverized Catalyst A, a back layer as the third layer was filled with 6 g of the pulverized Catalyst A, and the inert substance was filled from the location at 0.4 provided that the weight of the whole catalyst in the front layer and the back layer was 1.

An activity test was conducted in the same manner as Example 1 except that the molten salt bath was kept at 400° C. As a result, the meta-xylene conversion rate was 92% and the isophthalonitrile yield was 68%.

A hot spot having the highest temperature in the catalyst bed was caused in the first layer (front layer), and the temperature inside the catalyst bed became low in the second layer (inert substance layer) and became high and then low in the third layer (back layer). The hot spot temperature was 431° C. The results are summarized in Table 2 below.

Example 4

The catalyst bed was filled with a catalyst in the same manner as Example 2 except that another apparatus having the same dimensions as the apparatus used in Examples 1-3 was used in order to evaluate the change in the performance of the catalyst with time. Specifically, a front layer as the first layer was filled with 3 g of the pulverized Catalyst A, and a back layer as the third layer was filled with 7 g of the pulverized Catalyst A.

An activity test was conducted in the same manner as Example 1 except that the molten salt bath was kept at 406° C. As a result, the meta-xylene conversion rate was 90% and the isophthalonitrile yield was 68%.

The temperature inside the catalyst bed became high in the first layer (front layer), became low in the second layer (inert substance layer), and a hot spot having the highest temperature in the catalyst bed was caused in the third layer (back layer). The hot spot temperature was 433° C.

An activity test of the catalyst was conducted continuously under the same conditions for 240 days. As a result, the meta-xylene conversion rate was 91% and the isophthalonitrile yield was 69%, where the hot spot was still located in the third layer (back layer) and was 435° C. The results are summarized in Table 2 below.

Comparative Example 2

Figure 4:
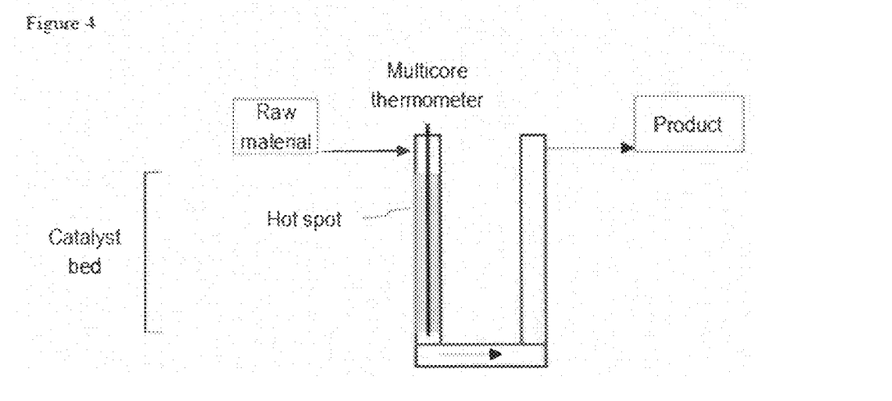
FIG. 4 A schematic view of a reaction tube used in Comparative example 2.

As shown in FIG. 4, a SUS304 U-shaped reaction tube having an inner diameter of 28 mm and a height of 4,000 mm was placed in a fluidized sand bath heating apparatus, where the descending section of the reaction tube on the inlet side served as a catalyst bed, and a multicore thermometer having an outer diameter of 6.8 mm was inserted into the reaction tube across the catalyst bed. Then, the catalyst bed was filled entirely with 1,410 g of Catalyst B.

While keeping the temperature of the sand bath at 384° C., raw materials, namely, meta-xylene at 170 g/hr, ammonia at 4.6 NL/min, air at 14 NL/min and nitrogen at 40 NL/min, were introduced into the reaction tube that maintained a gauge pressure of 80 kPa so as to allow contact reaction thereof. The resultant was analyzed in the same manner as Example 1. As a result, the meta-xylene conversion rate was 94% and the isophthalonitrile yield was 72%.

In the catalyst bed shown in FIG. 4, a hot spot occurred at the part indicated as so. The hot spot was located in the vicinity of 0.32 provided that the weight of the whole catalyst bed in the reaction tube was 1. The hot spot temperature, namely, the highest temperature of the catalyst bed was 427° C. The results are summarized in Table 3 below.

Example 5

Figure 5:
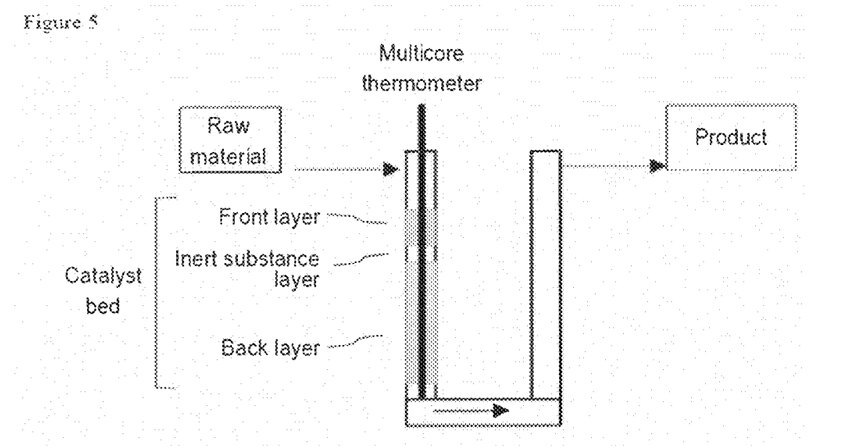
FIG. 5 A schematic view of a reaction tube used in Example 5.

As shown in FIG. 5, a SUS304 U-shaped reaction tube having an inner diameter of 28 mm and a height of 4,000 mm was placed in a fluidized sand bath heating apparatus, where the descending section of the reaction tube on the inlet side served as a catalyst bed, and a multicore thermometer having an outer diameter of 6.8 mm was inserted into the reaction tube across the catalyst bed.

Then, in the catalyst bed, a front layer as the first layer was filled with 360 g of Catalyst B, an inert substance layer as the second layer (corresponding to the hot spot site identified in Comparative example 2) was filled with 400 g of ceramic raschig rings as inert substance each having an outer diameter of 6 mm, an inner diameter of 3 mm and a height of 6 mm (manufactured by Sakaguchi E.H Voc Corp.), and a back layer as the third layer was filled with 980 g of Catalyst B. The inert substance was filled from the location at 0.27 provided that the weight of the whole catalyst in the front layer and the back layer was 1.

The temperature of the sand bath was kept at 385° C. while contact reaction took place in the same manner as Comparative example 2. The resultant was analyzed in the same manner as Comparative example 2. As a result, the meta-xylene conversion rate was 93% and the isophthalonitrile yield was 69%.

As to the temperature inside the catalyst bed, a hot spot having the highest temperature in the catalyst bed was caused in the first layer (front layer). The hot spot temperature was 411° C. The results are summarized in Table 3 below.

As can be appreciated from Examples 1-3 and Comparative example 1 that were filled with Catalyst A as well as Example 5 and Comparative example 2 that were filled with Catalyst B, the hot spot temperature became low by filling inert substance into the hot spot site. Furthermore, as can be appreciated from Example 4, a stable operation was realized for a long period of time.

Comparative Example 3

Figure 6:
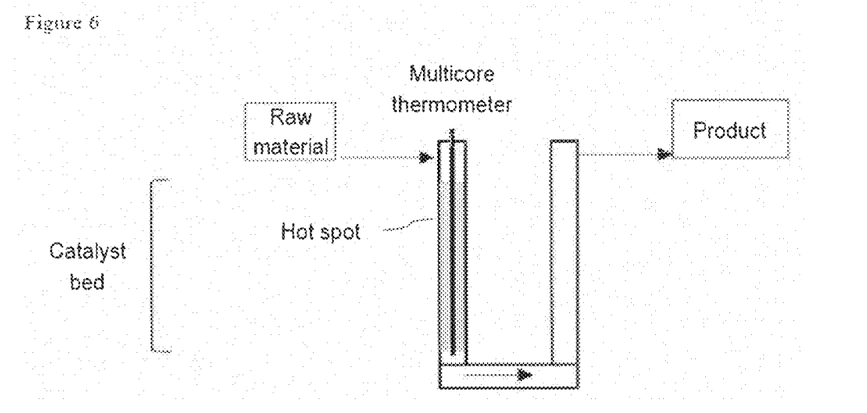
FIG. 6 A schematic view of a reaction tube used in Comparative example 3.

As shown in FIG. 6, a SUS304 U-shaped reaction tube having an inner diameter of 28 mm and a height of 4,000 mm was placed in a fluidized sand bath heating apparatus, where the descending section of the reaction tube on the inlet side served as a catalyst bed, and a multicore thermometer having an outer diameter of 6.8 mm was inserted into the reaction tube. Then, the catalyst bed was filled entirely with 1,300 g of Catalyst A.

While keeping the temperature of the sand bath at 378° C., raw materials, namely, meta-xylene at 170 g/hr, ammonia at 4.6 NL/min, air at 14 NL/min and nitrogen at 40 NL/min, were introduced into the reaction tube that maintained a gauge pressure of 80 kPa so as to allow contact reaction thereof. The resultant was analyzed in the same manner as Example 1. As a result, the meta-xylene conversion rate was 92% and the isophthalonitrile yield was 72%.

In the catalyst bed shown in FIG. 6, a hot spot occurred at the part indicated as so. The hot spot was located in the vicinity of 0.23 provided that the weight of the whole catalyst bed in the reaction tube was 1. The hot spot temperature, namely, the highest temperature of the catalyst bed was 423° C. The results are summarized in Table 4 below.

Example 6

Figure 7:
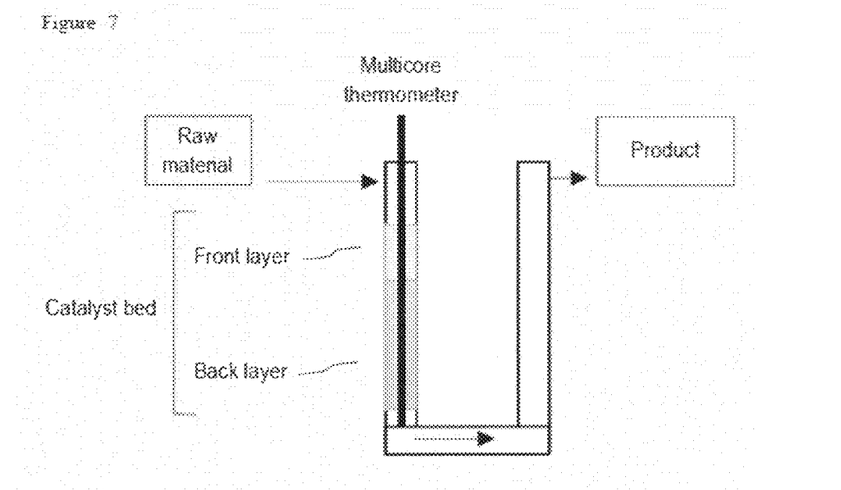
FIG. 7 A schematic view of a reaction tube used in Examples 6 and 7.

As shown in FIG. 7, a SUS304 U-shaped reaction tube having an inner diameter of 28 mm and a height of 4,000 mm was placed in a fluidized sand bath heating apparatus, where the descending section of the reaction tube on the inlet side served as a catalyst bed, and a multicore thermometer having an outer diameter of 6.8 mm was inserted into the reaction tube.

Then, 8 packs of a homogeneous mixture of 50 g of Catalyst A and 50 g of ceramic raschig rings as inert substance each having an outer diameter of 6 mm, an inner diameter of 3 mm and a height of 6 mm (manufactured by Sakaguchi E.H Voc Corp.) (a 1:1 (Catalyst A/inert substance) mixed catalyst) were prepared. In the catalyst bed, a front layer as the first layer (corresponding to the hot spot site identified in Comparative example 3) was filled with 800 g of the 1:1 (Catalyst A/inert substance) mixed catalyst, and a back layer as the second layer was filled with 900 g of Catalyst A. The 1:1 (Catalyst A/inert substance) mixed catalyst was filled from the inlet to the location at 0.47 provided that the weight of the whole catalyst in the front layer and the back layer was 1.

While keeping the temperature of the sand bath at 385° C., raw materials, namely, meta-xylene at 170 g/hr, ammonia at 4.6 NL/min, air at 14 NL/min and nitrogen at 40 NL/min, were introduced into the reaction tube that maintained a gauge pressure of 80 kPa so as to allow contact reaction thereof. An activity test was conducted in the same manner as Comparative example 3. As a result, the meta-xylene conversion rate was 92% and the isophthalonitrile yield was 70%.

As to the temperature inside the catalyst bed, a hot spot having the highest temperature in the catalyst bed was caused in the second layer (back layer). The hot spot temperature was 419° C. The results are summarized in Table 4 below.

Example 7

Six packs of a homogeneous mixture of 67 g of Catalyst A and 33 g of ceramic raschig rings as inert substance each having an outer diameter of 6 mm, an inner diameter of 3 mm and a height of 6 mm (manufactured by Sakaguchi E.H Voc Corp.) (a 2:1 (Catalyst A/inert substance) mixed catalyst) were prepared. In the catalyst bed of a reaction tube similar to Example 6, a front layer as the first layer (corresponding to the hot spot site identified in Comparative example 3) was filled with 600 g of the 2:1 (Catalyst A/inert substance) mixed catalyst, and a back layer as the second layer was filled with 900 g of Catalyst A. The 2:1 (Catalyst A/inert substance) mixed catalyst was filled from the inlet to the location at 0.40 provided that the weight of the whole catalyst in the front layer and the back layer was 1.

An activity test was conducted in the same manner as Example 6 except that the sand bath was kept at 384° C. As a result, the meta-xylene conversion rate was 93% and the isophthalonitrile yield was 70%.

As to the temperature inside the catalyst bed, a hot spot having the highest temperature in the catalyst bed was caused in the second layer (back layer). The hot spot temperature was 415° C. The results are summarized in Table 4 below.

As can be appreciated from Examples 6 and 7 and Comparative example 3, the hot spot temperature became low by filling a dual (inert substance-mixed Catalyst A/Catalyst A) catalyst.

Comparative Example 4

Figure 8:
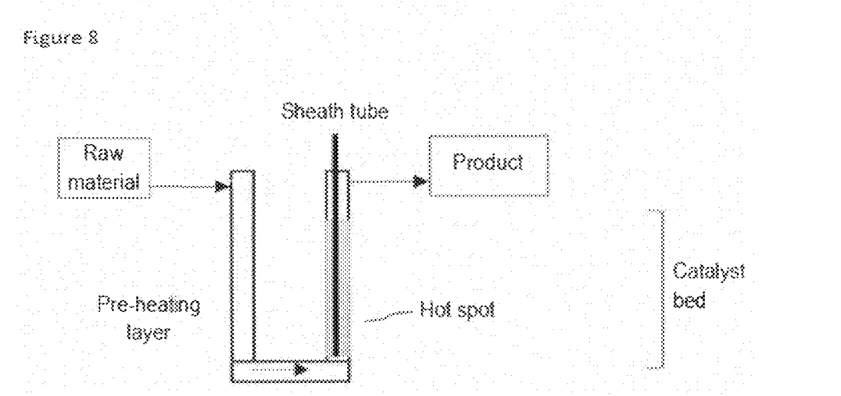
FIG. 8 A schematic view of a reaction tube used in Comparative example 4.

As shown in FIG. 8, a SUS304 U-shaped reaction tube having an inner diameter of 20 mm and a height of 500 mm was prepared, where the descending section of the reaction tube on the inlet side served as a pre-heating layer while the ascending section of the reaction tube on the outlet side served as a catalyst bed, and a sheath tube having an outer diameter of 2 mm was inserted therein so that a tip of a thermocouple can be moved up and down inside the reaction tube across the catalyst bed to measure the temperature thereof. Then, the catalyst bed was filled entirely with 20 g of the pulverized Catalyst A.

While keeping the temperature of the molten sand bath at 390° C., raw materials, namely, meta-xylene at 3.9 g/hr, ammonia at 4.9 g/hr, air at 310 Nml/min and nitrogen at 780 Nml/min, were introduced into the reaction tube at atmospheric pressure so as to allow contact reaction thereof. An activity test was conducted in the same manner as Example 1. As a result, the meta-xylene conversion rate was 91% and the isophthalonitrile yield was 62%.

In the catalyst bed shown in FIG. 8, a hot spot occurred at the part indicated as so. The hot spot was located in the vicinity of 0.25 provided that the weight of the whole catalyst bed in the reaction tube was 1. The hot spot temperature, namely, the highest temperature of the catalyst bed was 486° C. The results are summarized in Table 5 below.

Example 8

Figure 9:
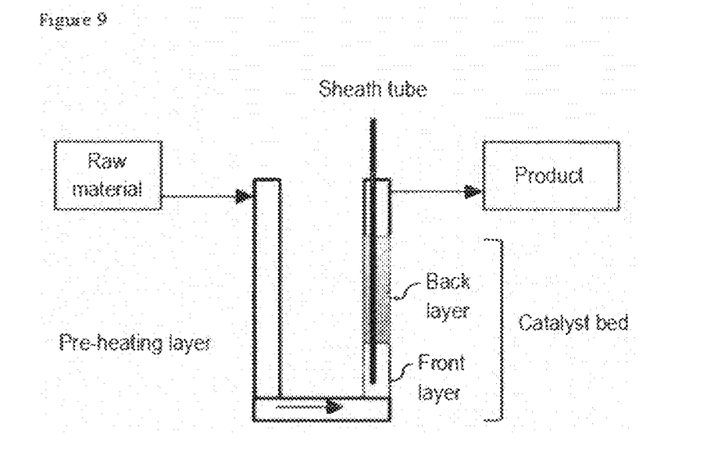
FIG. 9 A schematic view of a reaction tube used in Examples 8 and 9.

As shown in FIG. 9, a SUS304 U-shaped reaction tube having an inner diameter of 20 mm and a height of 500 mm was prepared, where the descending section of the reaction tube on the inlet side served as a pre-heating layer while the ascending section of the reaction tube on the outlet side served as a catalyst bed, and a sheath tube having an outer diameter of 2 mm was inserted therein so that a tip of a thermocouple can be moved up and down inside the reaction tube across the catalyst bed to measure the temperature thereof.

Next, Catalyst C (a boric acid-free catalyst) was pulverized into eight with pliers, and fractionated with a sieve having openings of 1.25 mm followed by another sieve having openings of 0.95 mm to prepare pulverized Catalyst C having sizes of 0.95-1.25 mm. The catalyst bed was filled with catalysts in the same manner as Example 6 except that a front layer as the first layer (corresponding to the hot spot site identified in Comparative example 4) was filled with 10 g of the pulverized Catalyst A, and a back layer as the second layer was filled with 10 g of the pulverized Catalyst C. Pulverized Catalyst A was filled from the inlet to the location at 0.5 provided that the weight of the whole catalyst in the front layer and the back layer was 1.

An activity test was conducted in the same manner as Example 6 except that the temperature of the sand bath was kept at 376° C., and raw materials, namely, meta-xylene at 3.9 g/hr, ammonia at 4.9 g/hr, air at 310 Nml/min and nitrogen at 780 Nml/min, were introduced into the reaction tube at atmospheric pressure so as to allow contact reaction thereof. As a result, the meta-xylene conversion rate was 92% and the isophthalonitrile yield was 64%.

As to the temperature inside the catalyst bed, a hot spot having the highest temperature in the catalyst bed was caused in the second layer (back layer). The hot spot temperature was 458° C. The results are summarized in Table 5 below.

Example 9

Catalyst D (a catalyst having high calcination temperature) was pulverized into eight with pliers, and then fractionated with a sieve having openings of 1.25 mm followed by another sieve having openings of 0.95 mm to prepare pulverized Catalyst D having sizes of 0.95-1.25 mm. The catalyst bed was filled with catalysts in the same manner as Example 8 except that a front layer as the first layer (corresponding to the hot spot site identified in Comparative example 4) was filled with 10 g of the pulverized Catalyst A, and a back layer as the second layer was filled with 10 g of the pulverized Catalyst D. Provided that the weight of the whole catalyst in the front layer and the back layer was 1, pulverized Catalyst A from the inlet to the location at 0.5.

An activity test was conducted in the same manner as Example 8 except that the temperature of the sand bath was kept at 384° C. As a result, the meta-xylene conversion rate was 91% and the isophthalonitrile yield was 64%.

As to the temperature inside the catalyst bed, a hot spot having the highest temperature in the catalyst bed was caused in the second layer (back layer). The hot spot temperature was 465° C. The results are summarized in Table 5 below.

As can be appreciated from Examples 8 and 9 and Comparative example 4, the hot spot temperature became low by filling a dual (Catalyst A/Catalyst C or Catalyst A/Catalyst D) catalyst.

TABLE 1

|  |  | Comparative example 1 | Example 1 | Example 2 |
|---|---|---|---|---|
| First layer (Front layer) | g | Pulverized 10 g Catalyst A | Pulverized Catalyst A 2 g | Pulverized Catalyst A 3 g |
| Second layer (Inert substance layer) | g |  | Ceramic raschig rings 12 g OD3 × ID1 × H2.5 mm | Ceramic raschig rings 12 g OD3 × ID1 × H2.5 mm |
| Third layer (Back layer) | g |  | Pulverized Catalyst A 8 g | Pulverized Catalyst A 7 g |
| Front layer/ (Front layer + Back layer) weight ratio |  | — | 0.20 | 0.30 |
| Inert substance/ (Inert substance + Catalyst) weight ratio |  | — | 0.55 | 0.55 |
| Control temperature | ° C. | 398 | 404 | 402 |
| Meta-xylene conversion rate | % | 91 | 92 | 91 |
| Isophthalonitrile yield | % | 71 | 69 | 68 |
| Hot spot location |  | 0.31 | Third layer | First layer |
| Hot spot temperature | ° C. | 447 | 439 | 429 |

TABLE 2

|  |  | Example 3 | Example 4 |
|---|---|---|---|
| First layer (Front layer) | g | Pulverized Catalyst A 4 g | Pulverized Catalyst A 3 g 240 days later |
| Second layer (Inert substance layer) | g | Ceramic raschig rings 12 g OD# × ID1 × H2.5 mm | Ceramic raschig rings 12 g OD3 × ID1 × H2.5 mm |
| Third layer (Back layer) | g | Pulverized Catalyst A 6 g | Pulverized Catalyst A 7 g |

TABLE 2-continued

|  |  | Example 3 | Example 4 |  |
|---|---|---|---|---|
| Front layer/(Front layer + Back layer) weight ratio |  | 0.40 | 0.30 | — |
| Inert substance/(Inert substance + Catalyst) weight ratio |  | 0.55 | 0.55 | — |
| Control temperature | °C. | 400 | 406 | 406 |
| Meta-xylene conversion rate | % | 92 | 90 | 91 |
| Isophthalonitrile yield | % | 68 | 68 | 69 |
| Hot spot location |  | First layer | Third layer | Third layer |
| Hot spot temperature | °C. | 431 | 433 | 435 |

TABLE 3

|  |  | Comparative example 2 | Example 5 |  |
|---|---|---|---|---|
| First layer (Front layer) | g | Catalyst B 1,410 g | Catalyst B | 360 g |
| Second layer (Inert substance layer) | g |  | Ceramic raschig rings OD6 × ID3 × H6 mm | 400 g |
| Third layer (Back layer) | g |  | Catalyst B | 980 g |
| Front layer/(Front layer + Back layer) weight ratio |  | — | 0.27 |  |
| Inert substance/(Inert substance + Catalyst) weight ratio |  | — | 0.23 |  |
| Control temperature | °C. | 384 | 385 |  |
| Meta-xylene conversion rate | % | 94 | 93 |  |
| Isophthalonitrile yield | % | 72 | 69 |  |
| Hot spot location |  | 0.32 | First layer |  |
| Hot spot temperature | °C. | 427 | 411 |  |

TABLE 4

|  |  | Comparative example 3 | Example 6 | Example 7 |
|---|---|---|---|---|
| First layer (Front layer) | g | Catalyst A 1,300 g | Catalyst A + Ceramic raschig rings OD6 × ID3 × H6 mm (=1:1) 800 g | Catalyst A + Ceramic raschig rings OD6 × ID3 × H6 mm (=2:1) 600 g |
| Second layer (Back layer) | g |  | Catalyst A 900 g | Catalyst A 900 g |
| Front layer/(Front layer + Back layer) weight ratio |  | — | 0.47 | 0.40 |
| Control temperature | °C. | 378 | 385 | 384 |
| Meta-xylene conversion rate | % | 92 | 92 | 93 |
| Isophthalonitrile yield | % | 72 | 70 | 70 |
| Hot spot location |  | 0.23 | Second layer | Second layer |
| Hot spot temperature | °C. | 423 | 419 | 415 |

TABLE 5

|  |  | Comparative example 4 | Example 8 | Example 9 |
|---|---|---|---|---|
| First layer (Front layer) | g | Pulverized Catalyst A 20 g | Pulverized Catalyst A 10 g | Pulverized Catalyst A 10 g |
| Second layer (Back layer) | g |  | Pulverized Catalyst C (boron free) 10 g | Pulverized Catalyst D (high calcination temperature) 10 g |
| Front layer/(Front layer + Back layer) weight ratio |  | — | 0.50 | 0.50 |

TABLE 5-continued

| | | Comparative example 4 | Example 8 | Example 9 |
|---|---|---|---|---|
| Control temperature | ° C. | 390 | 376 | 384 |
| Meta-xylene conversion rate | % | 91 | 92 | 91 |
| Isophthalonitrile yield | % | 62 | 64 | 64 |
| Hot spot location | | 0.25 | Second layer | Second layer |
| Hot spot temperature | ° C. | 486 | 458 | 465 |

The invention claimed is:

1. A method for producing an aromatic nitrile, the method comprising:
contacting a gaseous mixture comprising an aromatic hydrocarbon, ammonia, and oxygen with a catalyst within a fixed bed reactor comprising a plurality of reaction tubes to produce the corresponding aromatic nitrile,
wherein the catalyst comprises an oxide comprising vanadium, chromium, and boron, and at least one support selected from the group consisting of alumina, silica-alumina, zirconia, and titania, and
wherein one of the reaction tubes is filled with the catalyst to identify a site of a hot spot, and then, for each of the other reaction tubes, a part in each of the other reaction tubes corresponding at least to the hot spot is filled with an inert substance while a part other than that in each of the other reaction tubes is filled with the catalyst.

2. A method for producing an aromatic nitrile, the method comprising:
contacting a gaseous mixture comprising an aromatic hydrocarbon, ammonia, and oxygen with a catalyst within a fixed bed reactor comprising a plurality of reaction tubes to produce the corresponding aromatic nitrile,
wherein the catalyst comprises an oxide comprising vanadium, chromium, and boron, and at least one support selected from the group consisting of alumina, silica-alumina, zirconia, and titania, and
wherein one of the reaction tubes is filled with the catalyst to identify a site of a hot spot, and then, for each of the other reaction tubes, a part in each of the other reaction tubes corresponding at least to the hot spot is filled with a mixture of the catalyst and an inert substance while a part other than that in each of the other reaction tubes is filled with the catalyst.

3. A method for producing an aromatic nitrile, the method comprising:
contacting a gaseous mixture comprising an aromatic hydrocarbon, ammonia, and oxygen with a catalyst within a fixed bed reactor comprising a plurality of reaction tubes to produce the corresponding aromatic nitrile,
wherein the catalyst comprises an oxide comprising vanadium, chromium, and boron, and at least one support selected from the group consisting of alumina, silica-alumina, zirconia, and titania, and
wherein one of the reaction tubes is filled with the catalyst to identify a site of a hot spot, and then, for each of the other reaction tubes, a part in each of the other reaction tubes corresponding at least to the hot spot is filled with the catalyst while a part other than that in each of the other reaction tubes is filled with a catalyst free of boron or a catalyst having a lower concentration of boron than the catalyst.

4. A method for producing an aromatic nitrile, the method comprising:
contacting a gaseous mixture comprising an aromatic hydrocarbon, ammonia, and oxygen with a catalyst within a fixed bed reactor comprising a plurality of reaction tubes to produce the corresponding aromatic nitrile,
wherein the catalyst comprises an oxide comprising vanadium, chromium, and boron, and at least one support selected from the group consisting of alumina, silica-alumina, zirconia, and titania, and
wherein one of the reaction tubes is filled with the catalyst to identify a site of a hot spot, and then, for each of the other reaction tubes, a part in each of the other reaction tubes corresponding at least to the hot spot is filled a first catalyst while a part other than that in each of the other reaction tubes is filled with a second catalyst having a higher calcination temperature than the first catalyst, and
wherein the catalyst is the same as the first catalyst or the second catalyst, or is different from the first catalyst and the second catalyst.

5. The method for producing an aromatic nitrile according to claim 1, wherein the oxide comprising vanadium, chromium, and boron is represented by the following composition formula:

$$V_a Cr_b B_c X_d O_e,$$

wherein:
V represents vanadium,
Cr represents chromium,
B represents boron,
X represents one element selected from the group consisting of phosphorus, molybdenum, iron, tungsten, germanium, manganese, tin, tantalum, niobium, antimony, bismuth, lead, tellurium, cobalt, nickel, sodium, potassium, rubidium, cesium, magnesium, calcium, and barium,
O represents oxygen, and
subscripts a, b, c, d, and e represent the atomic ratios of respective elements,
where a is 1,
b is from 0.5 to 2.0,
c is from 0.01 to 1.5,
d is from 0 to 2.0, and
e represents the oxygen number corresponding to an oxide or a complex oxide formed by binding the elements.

6. The method for producing an aromatic nitrile according to claim 1, wherein the at least one support is titania.

7. The method for producing an aromatic nitrile according to claim 2, wherein the part corresponding at least to the hot spot comprises an inlet of the reaction tube to the hot spot.

8. The method for producing an aromatic nitrile according to claim 2, wherein an amount of the catalyst in the part corresponding at least to the hot spot is 0.6 or less provided that the weight of the entire catalyst bed in the reaction tube is 1.

9. The method for producing an aromatic nitrile according to claim 2, wherein the oxide comprising vanadium, chromium, and boron is represented by the following composition formula:

$$V_aCr_bB_cX_dO_e,$$

wherein:
V represents vanadium,
Cr represents chromium,
B represents boron,
X represents one element selected from the group consisting of phosphorus, molybdenum, iron, tungsten, germanium, manganese, tin, tantalum, niobium, antimony, bismuth, lead, tellurium, cobalt, nickel, sodium, potassium, rubidium, cesium, magnesium, calcium, and barium,
O represents oxygen, and
subscripts a, b, c, d, and e represent the atomic ratios of respective elements,
where a is 1,
b is from 0.5 to 2.0,
c is from 0.01 to 1.5,
d is from 0 to 2.0, and
e represents the oxygen number corresponding to an oxide or a complex oxide formed by binding the elements.

10. The method for producing an aromatic nitrile according to claim 3, wherein the oxide comprising vanadium, chromium, and boron is represented by the following composition formula:

$$V_aCr_bB_cX_dO_e,$$

wherein:
V represents vanadium,
Cr represents chromium,
B represents boron,
X represents one element selected from the group consisting of phosphorus, molybdenum, iron, tungsten, germanium, manganese, tin, tantalum, niobium, antimony, bismuth, lead, tellurium, cobalt, nickel, sodium, potassium, rubidium, cesium, magnesium, calcium, and barium,
O represents oxygen, and
subscripts a, b, c, d, and e represent the atomic ratios of respective elements, where a is 1,
b is from 0.5 to 2.0,
c is from 0.01 to 1.5,
d is from 0 to 2.0, and
e represents the oxygen number corresponding to an oxide or a complex oxide formed by binding the elements.

11. The method for producing an aromatic nitrile according to claim 4, wherein the oxide comprising vanadium, chromium, and boron is represented by the following composition formula:

$$V_aCr_bB_cX_dO_e,$$

wherein:
V represents vanadium,
Cr represents chromium,
B represents boron,
X represents one element selected from the group consisting of phosphorus, molybdenum, iron, tungsten, germanium, manganese, tin, tantalum, niobium, antimony, bismuth, lead, tellurium, cobalt, nickel, sodium, potassium, rubidium, cesium, magnesium, calcium, and barium,
O represents oxygen, and
subscripts a, b, c, d, and e represent the atomic ratios of respective elements,
where a is 1,
b is from 0.5 to 2.0,
c is from 0.01 to 1.5,
d is from 0 to 2.0, and
e represents the oxygen number corresponding to an oxide or a complex oxide formed by binding the elements.

12. The method for producing an aromatic nitrile according to claim 2, wherein the at least one support is titania.

13. The method for producing an aromatic nitrile according to claim 3, wherein the at least one support is titania.

14. The method for producing an aromatic nitrile according to claim 4, wherein the at least support is titania.

15. The method for producing an aromatic nitrile according to claim 3, wherein the part corresponding at least to the hot spot comprises an inlet of the reaction tube to the hot spot.

16. The method for producing an aromatic nitrile according to claim 4, wherein the part corresponding at least to said hot spot comprises an inlet of the reaction tube to the hot spot.

17. The method for producing an aromatic nitrile according to claim 3, wherein an amount of the catalyst in the part corresponding at least to the hot spot is 0.6 or less provided that the weight of the entire catalyst bed in the reaction tube is 1.

18. The method for producing an aromatic nitrile according to claim 4, wherein an amount of the catalyst in the part corresponding at least to the hot spot is 0.6 or less provided that the weight of the entire catalyst bed in the reaction tube is 1.

* * * * *